United States Patent
Richter

[11] 3,982,019
[45] Sept. 21, 1976

[54] INSECTICIDAL COMPOSITIONS CONTAINING TRIFLUOROMETHYL UREAS AND METHOD OF CONTROLLING INSECTS USING SAID COMPOSITIONS

[75] Inventor: Sidney B. Richter, Chicago, Ill.

[73] Assignee: Velsicol Chemical Corporation, Chicago, Ill.

[22] Filed: Feb. 18, 1975

[21] Appl. No.: 545,651

Related U.S. Application Data

[62] Division of Ser. No. 745,384, July 17, 1968, Pat. No. 3,895,061.

[52] U.S. Cl. .................................. 424/322; 424/302
[51] Int. Cl.² ................................................ A01N 9/20
[58] Field of Search ................... 424/322, 302, 304

[56] References Cited
UNITED STATES PATENTS

| | | | |
|---|---|---|---|
| 3,230,141 | 1/1966 | Frick et al. .......................... | 424/322 |
| 3,546,344 | 12/1970 | Martin et al. ........................ | 424/302 |

*Primary Examiner*—Glennon H. Hollrah
*Attorney, Agent, or Firm*—Robert J. Schwarz; Dietmar H. Olesch

[57] ABSTRACT

New chemical compositions of the formula:

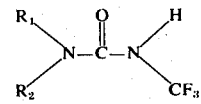

wherein $R_1$ is selected from the group consisting of alkyl, alkenyl, cycloalkyl and

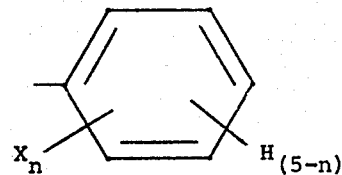

wherein X is selected from the group consisting of alkyl, alkenyl, halogen, alkoxy, alkylthio, dialkylamino, nitro, cyano and thiocyano, and $n$ is an integer from 0 to 5; and $R_2$ is selected from the group consisting of hydrogen and $R_1$. An insecticidal and herbicidal composition comprising an inert carrier and, as an essential active ingredient, in a quantity toxic to insects and weeds a compound described above.

2 Claims, No Drawings

INSECTICIDAL COMPOSITIONS CONTAINING TRIFLUOROMETHYL UREAS AND METHOD OF CONTROLLING INSECTS USING SAID COMPOSITIONS

This application is a division of copending application Ser. No. 745,384, filed July 17, 1968 now U.S. Pat. No. 3,895,061, issued July 15, 1975.

This invention relates to new compositions of matter, and more particularly relates to new chemical compounds of the formula

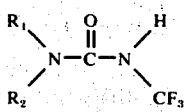

wherein $R_1$ is selected from the group consisting of alkyl, alkenyl, cycloalkyl and

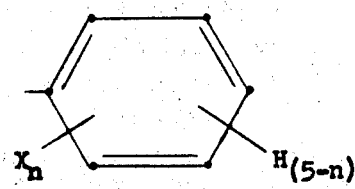

wherein X is selected from the group consisting of alkyl, alkenyl, halogen, alkoxy, alkylthio, dialkylamino, nitro, cyano and thiocyano, and $n$ is an integer from 0 to 5; and $R_2$ is selected from the group consisting of hydrogen and $R_1$.

In a preferred embodiment of this invention the substituent $R_1$ is selected from the group consisting of alkyl having up to ten carbon atoms, alkenyl having up to 10 carbon atoms, cycloalkyl having from 4 to 8 carbon atoms and

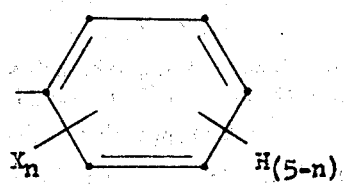

wherein the X substituent is selected from the group consisting of lower alkyl, lower alkenyl, chlorine, bromine, lower alkoxy, lower alkylthio, di(lower alkyl)amino, nitro, cyano and thiocyano; $n$ is an integer from 0 to 3; and $R_2$ is selected from the group consisting of hydrogen and the preferred $R_1$.

The compounds of the present invention are useful as pesticides particularly as insecticides and herbicides.

The compounds of the present invention can be readily prepared by reacting a primary or secondary amine of the formula

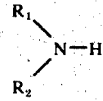

wherein $R_1$ and $R_2$ are as hereinabove described, with an equimolar amount of trifluoromethyl isocyanate. This reaction can be carried out by charging the amine or a solution of the amine in a suitable inert organic solvent, such as toluene, into a reaction vessel and then adding the trifluotomethyl isocyanate thereto. The reaction can be performed at atmospheric pressure by bubbling the trifluoromethyl isocyanate into the reaction medium, with vigorous stirring at room temperature, or at superatmospheric pressures in a sealed reaction vessel. A convenient manner in which to effect this reaction is in a closed system by either adding the trifluoromethyl isocyanate under pressure or by first cooling the amine to a temperature below about −40° C., adding the isocyanate, and then sealing the reaction vessel. In many instances this reaction is sufficiently exothermic to require intermittent cooling during the reaction. After the reaction is completed the desired product can be recovered by stripping the solvent if used, and can be purified by distilling the product if it is a liquid, or by triturating, recrystallizing or other common methods in the art if the product is a solid.

Exemplary of suitable primary and secondary amines for the purpose of preparing the compounds of the present invention are methylamine, ethylamine, n-propylamine, isopropylamine, butylamine, pentylamine, decylamine, dimethylamine, N-methyl-N-allylamine, diethylamine, allylamine, N-methyl-N-ethylamine, di-n-propylamine, 2-butenylamine, aniline, N-methylaniline, N-ethylaniline, N-isopropylaniline, N-n-butylaniline, 3-chloroaniline, 4-chloroaniline, 2,4-dimethylaniline, N2,4-trimethylaniline, 4-nitroaniline, 3,4-dichloroaniline, 3-methyl-4-chloroaniline, 4-dimethylaminoaniline, 2-methoxyaniline, N-isopropyl-2,4-dichloroaniline, N-methyl-o-toluidine, m-toluidine, p-toluidine, 2-methoxy-4-chloroaniline, N,N-diphenylaniline, 3-methylthioaniline, N-methyl-2-chloro-4-nitroaniline, 3-cyanoaniline, 4-thiocyanoaniline, N-phenyl-N-3,4-dichloroaniline, cyclohexylamine, N-methyl-N-cyclohexylamine, N-ethyl-N-cyclohexyl-amine, N-isopropyl-N-cyclohexylamine, N-allyl-N-cyclohexylamine, N-n-pentyl-N-cyclohexylamine and the like.

The manner is which the compounds of this invention can be prepared readily is illustrated in the following examples.

EXAMPLE 1

Preparation of N-Methyl-N'-trifluoromethyl Urea

Methylamine (3.1 grams; 0.1 mol) is placed into a glass ampule of 30 ml capacity and is cooled in an acetone-dry ice bath. Trifluoromethyl isocyanate (11.1 grams; 0.1 mol) is added to the ampule and the ampule is sealed. The reaction mixture is slowly warmed up to room temperature and is allowed to stand at this temperature for a period of about 1 hour. At the end of this time the ampule is opened and the contents removed and distilled under reduced pressure to yield N-methyl-N'-trifluoromethyl urea.

EXAMPLE 2

Preparation of N,N-Diethyl-N'-trifluoromethyl Urea

Dimethylamine (4.9 grams; 0.1 mol) is placed into a glass ampule of 30 ml capacity and is cooled in an acetone-dry ice bath. Trifluoromethyl isocyanate (11.1 grams; 0.1 mol) is added to the ampule and the ampule is sealed. The reaction mixture is slowly warmed up to room temperature and is allowed to stand for a period of about 1 hour. After this time the ampule is opened and its contents removed and distilled under reduced pressure to yield N,N-diethyl-N'-trifluoromethyl urea.

EXAMPLE 3

Preparation of N-Phenyl-N'-trifluoromethyl Urea

A solution of aniline (93.12 grams; 1.0 mol) in toluene (200 ml) is charged into a glass reaction flask equipped with a mechanical stirrer, thermometer and gas inlet tube. Trifluoromethyl isocyanate (111 grams; 1.0 mol) is slowly bubbled into the reaction medium with vigorous stirring. The temperature of the reaction mixture is kept below about 50° C. After the addition is completed the reaction mixture is stirred for an additional period of about 1 hour. After this time the toluene is stripped from the reaction mixture under reduced pressure. The residue is then recrystallized to yield N-phenyl-N'-trifluoromethyl urea.

EXAMPLE 4

Preparation of N-Phenyl-N-isopropyl-N'-trifluoromethyl Urea

A solution of N-methylaniline (10.7 grams; 0.1 mol) in toluene (100 ml) is charged into a glass reaction flask equipped with stirrer, thermometer and gas inlet tube. Trifluoromethyl isocyanate (11.1 grams; 0.1 mol) is slowly bubbled into the reaction medium with vigorous stirring and sufficient cooling to keep the temperature of the reaction mixture below about 50° C. After the addition is completed the reaction mixture is stirred for an additional period of about 1 hour. After this time the toluene is stripped from the reaction mixture under reduced pressure. The residue is then recrystallized to yield N-phenyl-N-isopropyl-N'-trifluoromethyl urea.

EXAMPLE 5

Preparation of N-(4-Chlorophenyl)-N'-trifluoromethyl Urea

A solution of 4-chloroaniline (64 grams; 0.5 mol) in toluene (100 ml) is placed into a suitable pressure vessel, and is cooled in an acetone-dry ice bath. Trifluoromethyl isocyanate (56 grams; 0.5 mol) is added thereto and the pressure vessel is sealed. The reaction mixture is allowed to warm up to room temperature and stand for a period of about 24 hours. After this time the pressure vessel is opened and the contents are stripped of toluene under reduced pressure. The residue is recrystallized to yield N-(4-chlorophenyl)-N'-trifluoromethyl urea.

EXAMPLE 6

Preparation of N-(3-methyl-4-chloro-phenyl)-N'-trifluoromethyl Urea

A solution of 3-methyl-4-chloroaniline (70 grams; 0.5 mol) in toluene (150 ml) is placed into a pressure vessel, and is cooled in an acetone-dry ice bath. Trifluoromethyl isocyanate (56 grams; 0.5 mol) is added and the pressure vessel is sealed. The reaction mixture is warmed to about 25° C. and is allowed to stand for about 24 hours. After this time the reaction vessel is opened and its contents are stripped of toluene by evaporation under reduced pressure. The residue is then recrystallized to yield N-(3-methyl-4-chlorophenyl)-N'-trifluoromethyl urea.

Other compounds within the scope of this invention can be prepared by the procedures described in the foregoing examples. Presented in the following examples are the essential ingredients required to prepare the indicated named compounds according to the procedures heretofore described.

EXAMPLE 7

Allylamine + trifluoromethyl isocyanate = N-allyl-N'-trifluoromethyl urea.

EXAMPLE 8

N-Methyl-N-allylamine + trifluoromethyl isocyanate = N-methyl-N-allyl-N'-trifluoromethyl urea.

EXAMPLE 9

N-Methyl-o-toluidine + trifluoromethyl isocyanate = methyl-N-(2-methylphenyl)-N'-trifluoromethyl urea.

EXAMPLE 10

N,N-Diphenylamine + trifluoromethyl isocyanate = N,N-diphenyl-N'-trifluoromethyl urea.

EXAMPLE 11

2-Methoxyaniline + trifluoromethyl isocyanate = N-(2-methoxyphenyl)-N'-trifluoromethyl urea.

EXAMPLE 12

2-Nitroaniline + trifluoromethyl isocyanate = N-(4-nitrophenyl)-N'-trifluoromethyl urea.

EXAMPLE 13

4-Cyanoaniline + trifluoromethyl isocyanate = N-(4-cyanophenyl)-N'-trifluoromethyl urea.

EXAMPLE 14

N-Isopropyl-4-dimethylaminoaniline + trifluoromethyl isocyanate = N-isopropyl-N-(4-dimethylaminophenyl)-N'-trifluoromethyl urea.

EXAMPLE 15

3-Thiocyanoaniline + trifluoromethyl isocyanate = N-(3-thiocyanophenyl)-N'-trifluoromethyl urea.

EXAMPLE 16

N-Methyl-4-methylthioaniline + trifluoromethyl isocyanate = N-methyl-N-(4-methylthiophenyl)-N'-trifluoromethyl urea.

EXAMPLE 17

Cyclohexylamine + trifluoromethyl isocyanate = N-cyclohexyl-N'-trifluoromethyl urea.

EXAMPLE 18

N-Methyl-N-cyclohexylamine + trifluoromethyl isocyanate = N-methyl-N-cyclohexyl-N'-trifluoromethyl urea.

Additional compounds within the scope of this invention which can be prepared by the procedures described in the preceding examples are:

N-n-butyl-N'-trifluoromethyl urea
N-octyl-N'-trifluoromethyl urea
N-decyl-N'-trifluoromethyl urea
N-cyclobutyl-N'-trifluoromethyl urea
N-cyclopentyl-N'-trifluoromethyl urea
N-cyclooctyl-N'-trifluoromethyl urea N-3-pentenyl-N'-trifluoromethyl urea
N-2-octenyl-N'-trifluoromethyl urea
N-(4-t-butylphenyl)-N'-trifluoromethyl urea
N-(3-iodophenyl)-N'-trifluoromethyl urea
N-(4-fluorophenyl)-N'-trifluoromethyl urea
N-(3-ethoxyphenyl)-N-methyl-N'-trifluoromethyl urea
N-(4-n-pentyloxphenyl)-N'-trifluoromethyl urea
N-(3-ethylthiophenyl)-N'-trifluoromethyl urea
N-(3-n-butylthiophenyl)-N'-trifluoromethyl urea
N-(4-decylthiophenyl)-N'-trifluoromethyl urea
N-(2-diethylaminophenyl)-N'-trifluoromethyl urea
N-(4-di-n-butylaminophenyl)-N'-trifluoromethyl urea
N-(4-di-n-pentylaminophenyl)-N'-trifluoromethyl urea The above compounds are presented in the way of examples and are not to be construed as limiting the scope of the present invention thereto.

For practical use as pesticides, the compounds of this invention are generally incorporated into pesticidal compositions which comprise an inert carrier and a pesticidally toxic amount of such a compound. Such pesticidal compositions, which can also be called formulations, enable the active compound to be applied conveniently to the site of the pest infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of pesticides can be dispersed under superatmospheric pressure as aerosols. However, preferred liquid pesticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the pest infestation. The emulsifiers most commonly used in these concentrates are nonionic or mixtures of non-ionic with anionic surface-active agents.

A typical pesticidal composition according to this invention is illustrated by the following example, in which the quantities are in parts by weight.

EXAMPLE 19

Preparation of a Dust

| Product of Example 1 | 10 |
|---|---|
| Powdered talc | 90 |

The above ingredients are mixed in a mechanical grinder-blender and are ground until a homogeneous, free-flowing dust of the desired particle size is obtained. This dust is suitable for direct application to the site of the pest infestation.

When used as insecticides the compounds of this invention can be applied in any manner recognized by the art. One method for destroying insects comprises applying to the locus of the insect infestation, an insecticidal composition comprising an inert carrier and as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal composition will comprise from about 5 to 75 percent by weight of the active compound. The compositions can also comprise such additional substances as other pesticides, stabilizers, spreaders, deactivators, adhesives, stickers, fertilizers, activators, synergists, and the like.

The compounds of the present invention are also useful when combined with other insecticides in the insecticidal compositions heretofore described. These other insecticides can comprise from about 5% to about 95% of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol, and the like; organic phosphorus compounds such as TEPP, schradan, ethion, parathion, methyl parathion, EPN, demeton, carbonphenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP, and the like; organic nitrogen compounds such as dinitro-o-cresol, dinitrocyclohexylphenol, DNB, DNP, binapacril, azobenzene, and the like; organic carbamate compounds such as carbaryl, ortho 5353, and the like; organic sulfur compounds such as phenothiazine, phenoxathin, lauryl thiocyanate, [bis(2-thiocyanoethyl)ether], isobornyl thiocyanoacetate, and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene, and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like;

while examples of nematodicidal compounds are chloropicrin, O,O-diethyl O-(2,4-dichlorophenyl) phosphorothioate, tetrachlorothiophene, dazomet, dibromochloropropane, and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects such as the Mexican bean beetle, the southern armyworm; the piercing-sucking insects, such as the pea aphid, the cereal leaf beetle, the house fly, the grape leafhopper, the chinch bug, the lygus bugs, osyter shell scale, the California red scale, the Florida red scale, the soft scale and mosquitoes; the internal feeders, including borers such as the European corn borer, the peach twig borer and the corn earworm, worms or weevils such as the codling moth, alfalfa weevil, cotton boll weevil, pink boll worm, plum curculio, red banded leaf roller, melonworm, cabbage looper and apple maggot, leaf miners such as the apple leaf miner, birch leaf miner and beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

Mites and ticks are not true insects. Many economically important species of mites and ticks can be controlled by the compounds of this present invention such as the red spider mite, the two spotted mite, the strawberry spider mite, the citrus rust mite, the cattle tick, the poultry mite, the citrus red mite and the European red mite. Chemicals useful for the control of mites are often called miticides, while those useful for the control of both mites and ticks are known specifically as acaricides.

The quantity of active compound of this invention to be used for insect control will depend on a variety of factors, such as the specific insect involved, intensity of the infestation, weather, type of environment, type of formulation, and the like. For example, the application of only one or two ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal utility of the compounds of the present invention can be demonstrated in a variety of experiments well known in the art. For example, the effectiveness of the compounds of this invention for the control of the common housefly (*Musca domestica*) can be shown in an experiment wherein the test compounds are formulated as aqueous emulsions of acetone solution and are then sprayed on fifty adult flies which have been placed into screen cages. The mortality of the flies is then determined after a period of 48 hours and rated in comparison with untreated controls. The results of this experiment demonstrate the utility of the compounds of this invention as insecticides.

When used as herbicides the compounds of this invention can be applied in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atratone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloroacetyl) piperidine, and the like; chlorinated aliphatic acid herbicides such as TCA, dalapon, 2,3-dichloropropionic acid, 2,2, 3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biruet, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, O-S-dimethyl tetrachlorothioterephthalate, methyl 2,3, 5,6-tetrachloro-N-methoxy-N-methyl-terephthalamate, 2-[(4-chloro-o-tolyl)-oxy]-N-methoxyacetamide, DSMA, MSMA, potassium azide, acrolein, benefin, bensulide, AMS, bromacil, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, bromihil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose-grass, chickweed, wild oats, velvet leaf, purselane, barnyard grass, smartweed, knotweed, cocklebur, wild buckwheat, kochia, medic, corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, round-leaved mallow, bull thistle, hounds-tongue, moth mullein, and purple star thistle; or perennials such as white cockle, perennial rye-grass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and winter-cress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention can be demonstrated by experiments carried out for the pre-emergence control of a variety of weeds. In these experiments small plastic greenhouse pots filled with dry soil are seeded with the weed seeds. Twenty-four hours or less after seeding the pots are sprayed with water until the soil is wet and the test compounds, formulated as aqueous emulsions of acetone solutions containing emulsifiers, are sprayed on the surface of the soil.

After spraying, the soil containers are placed in the greenhouse and provided with supplementary heat as required and daily or more frequent watering. The plants are maintained under these conditions for a period of from 15 to 21 days, at which time the condition of the plants and the degree of injury to the plants is rated on a scale of from 0 to 10, as follows: 0 = no injury, 1,2 = slight injury, 3,4 = moderate injury, 5,6 = moderately severe injury, 7,8,9 = severe injury and 10 = death. The results of these experiments demonstrate the effectiveness of these compounds as herbicides.

The herbicidal activity of the compounds of this invention can also be demonstrated by experiments carried out for the post-emergence control of various weeds. In these experiments the compounds to be tested are formulated as aqueous emulsions and sprayed on the foliage of the weeds that have attained a prescribed size. After spraying, the plants are placed in a greenhouse and watered daily or more frequently. Water is not applied to the foliage of the treated plants. The severity of the injury is determined 10 to 15 days after treatment and is rated on the scale of from 0 to 10 heretofore described. The effectiveness of these compounds as herbicides is demonstrated by the results of this experiment.

I claim:

1. An insecticidal composition comprising an inert carrier and, in a quantity toxic to insects, a compound of the formula

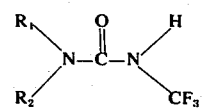

wherein $R_1$ is selected from the group consisting of alkyl having up to 10 carbon atoms, alkenyl having up to 10 carbon atoms, cycloalkyl having from 4 to 8 carbon atoms and

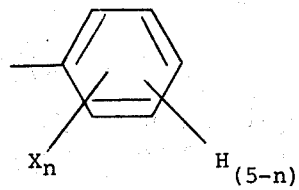

wherein X is selected from the group consisting of lower alkyl, lower alkenyl, chlorine, bromine, lower alkoxy, lower alkylthio, di (lower alkyl) amino, nitro, cyano and thiocyano; $n$ is an integer from 0 to 3; and $R_2$ is selected from the group consisting of hydrogen and $R_1$.

2. A method for the control of insects which comprises applying to said insects an effective amount of an insecticidal composition of claim 1.

* * * * *